US008830574B2

(12) United States Patent
Tafas

(10) Patent No.: US 8,830,574 B2
(45) Date of Patent: Sep. 9, 2014

(54) SYSTEM FOR READ-WRITE CONTROL OF SPECIMEN ANALYSIS BY AUTOMATED MICROSCOPE

(75) Inventor: Triantafyllos Tafas, Rocky Hill, CT (US)

(73) Assignee: Ikonisys, Inc., New Haven, CT (US)

( * ) Notice: Subject to any disclaimer, the term of this patent is extended or adjusted under 35 U.S.C. 154(b) by 0 days.

(21) Appl. No.: 12/566,961

(22) Filed: Sep. 25, 2009

(65) Prior Publication Data

US 2010/0046068 A1 Feb. 25, 2010

Related U.S. Application Data

(63) Continuation of application No. 11/685,140, filed on Mar. 12, 2007, now Pat. No. 7,706,061.

(60) Provisional application No. 60/781,768, filed on Mar. 13, 2006.

(51) Int. Cl.
| | |
|---|---|
| G02B 21/34 | (2006.01) |
| G02B 21/36 | (2006.01) |
| B01L 9/00 | (2006.01) |
| G01N 35/00 | (2006.01) |
| G01N 1/31 | (2006.01) |
| G01N 1/28 | (2006.01) |

(52) U.S. Cl.
CPC ........ *G02B 21/34* (2013.01); *G01N 2035/0091* (2013.01); *G01N 1/312* (2013.01); *G01N 35/00029* (2013.01); *G01N 2035/00089* (2013.01); *G01N 2035/00138* (2013.01); *G01N 2035/00782* (2013.01); *G02B 21/365* (2013.01); *B01L 9/52* (2013.01); *G01N 2035/00851* (2013.01); *G01N 2001/282* (2013.01)
USPC .......................................................... 359/396

(58) Field of Classification Search
None
See application file for complete search history.

(56) References Cited

U.S. PATENT DOCUMENTS

| | | |
|---|---|---|
| 4,248,498 A | 2/1981 | Georges |
| 4,367,915 A | 1/1983 | Georges |
| 5,561,556 A * | 10/1996 | Weissman ..................... 359/396 |
| 6,847,481 B1 | 1/2005 | Ludl et al. |
| 2002/0030598 A1* | 3/2002 | Dombrowski et al. .... 340/572.1 |
| 2003/0099580 A1 | 5/2003 | Pressman et al. |
| 2005/0051614 A1* | 3/2005 | Albany ......................... 235/375 |
| 2007/0279735 A1* | 12/2007 | Sieckmann ................... 359/396 |

FOREIGN PATENT DOCUMENTS

WO   WO 9910763 A1 *  3/1999

OTHER PUBLICATIONS

PCT International Search Report for PCT/US2007/063829, International Filing Date Mar. 12, 2007.

* cited by examiner

*Primary Examiner* — Arnel C Lavarias
(74) *Attorney, Agent, or Firm* — Kelley Drye & Warren LLP

(57) ABSTRACT

A system for automated microscopic analysis of a plurality of data-encoded microscope slides that provides that data written to or read from the slides may include images, analysis protocols, analytic results and other pertinent data. The system may also encompass a magazine that contains a plurality of data encoded slides.

8 Claims, 3 Drawing Sheets

SYSTEM FOR READ-WRITE CONTROL OF SPECIMEN ANALYSIS BY AUTOMATED MICROSCOPE

CROSS REFERENCE TO RELATED APPLICATIONS

This application is a continuation application that claims the benefit of co-pending U.S. non-provisional application Ser. No. 11/685,140, filed Mar. 12, 2007, which claims priority from U.S. provisional patent application Ser. No. 60/781,768, filed Mar. 13, 2006. The disclosure of such application is hereby incorporated by reference in its entirety where appropriate for teachings of additional or alternative details, features, and/or technical background, and from which priority is asserted.

BACKGROUND OF THE INVENTION

1. Field of the Invention

The present invention generally relates to a system for reading microscope slides in an automated fashion.

2. Description of the Related Art

Conventional biomedical microscopy generally has entailed laborious preparation of samples from a patient onto microscope slides followed by the sequential evaluation of each slide by a microscopist to determine if the patient samples indicate a biomedical condition. The process of evaluating slides is not only costly, but expends valuable time delaying treatment of biomedical maladies that may be detected.

One means for improving the efficiency of microscopy is to automate the process of presenting the slides for analysis under the microscope. A possible approach to this automation is taught by Georges in U.S. Pat. Nos. 4,248,498 and 4,367,915, both entitled Automatic Microscope Slide. The mechanism disclosed there includes the microscope slides removably housed in a storage magazine, and a first actuator mechanism which removes each slide, in succession, from the magazine. The slide thus removed is directly positioned for microscopic viewing by an XYZ stage. After viewing, the slide is automatically replaced to its original position in the slide magazine by a second actuator. The magazine is repositioned for access to the next slide, to be examined, and the process is repeated. The identification of the slide is determined solely by its location in the magazine. Any data associated with a given slide is separately recorded and associated with the slide only by means of reference to the slide's address location in the magazine. U.S. Pat. Nos. 4,248,498 and 4,367,915 do not address means for uniquely identifying slides which are not placed in their assigned locations or insuring linkage of the slide with its separately recorded data. Further, the location of regions of interest on the slide are not directly addressable; position data is only determinable for the slide holder.

SUMMARY OF INVENTION

There is disclosed herein a system for improving the efficiency of reading tissue sample slides.

In one embodiment there is disclosed a method in a computer system for automating microscopic analysis of a plurality of data-encoded microscope slides having material of analytical interest deposited thereon, and stored in a slide cassette, the method comprising: (a) determining the number and position of microscope slides stored in cassette; (b) causing one or more of slides in said cassette to be removed from cassette; (c) downloading encoded data on each of slide(s) removed from cassette; (d) associating said downloaded encoded data with a set protocol for analysis of said material on said microscope slide. The encoded data may comprise data physically stored on the slide, or in electronics associated with the slide.

In another embodiment, there is disclosed a slide magazine cassette for storing microscope slides, the magazine comprising: (a) a housing comprising a top surface, a bottom surface, and two side surfaces, surfaces defining a through-void there between; (b) a plurality of paired engagement structures attached to each of side surfaces of housing and projecting into thorough-void, each of paired engaging structures being substantially parallel to another pair of engaging structures attached to the antipodal side surface; wherein each of parallel paired engaging structures are configured and spaced to allow for the engagement and support of a single microscope slide between the engaging structures, and to permit movement of slide with respect to the engagement structures when a force is applied perpendicular to a parallel pair of engagement structures from either side of through-void.

The slides of such cassettes may be read by an automated unloading mechanism. In one embodiment, there is disclosed a slide feeder for moving slides housed in a microscope slide magazine/cassette. More generically there is disclosed a slide feeder for moving a slide having a top surface, a bottom surface and two or more lateral side surfaces(s) from a first location to a second location, the slide feeder comprising: a stage operatively configured to move in an x-y direction, and a slide engager coupled to the stage; the slide engager operatively configured to hold the slide by pressure fit between two or more lateral surfaces of the slide.

The slide feeder may feed a slide to a stage for reading. In an embodiment of the invention the microscope comprises multiple stages. In one embodiment, there is a first stage operatively configured to hold a microscope slide and to move only along an x-y axis, as well as a second stage operatively associated with the first stage and capable of movement only along the z.sup.—z.sup.+axis. In such embodiment movement of the second stage along such axis causes movement of the microscope slide held by the first stage in the same direction.

Reading of the samples on the slides may be improved by incorporating one or more coordinate reference points on the slides that are detectable by the microscopy system. In one embodiment there is disclosed an automated microscope slide analysis system for viewing microscope slides, the system comprising: (a) one or more microscope slides having one or more electronically-addressable position tag(s) thereon; (b) a field objective operatively configured to allow viewing of a defined field on microscope slide; (c) an emitter operatively configured to emit an electromagnetic wave toward at least one of electronically-addressable position tag(s); (d) a detector operatively configured to detect at least one of position tag(s) from the response of the tag to the electromagnetic wave, and a processor configured for processing information from the detector and the field objective to determine the position of the field viewed or desired to be marked with respect to at least one of the electronically-addressable position tag(s).

In one embodiment, the slide is imaged by a microscope slide image capture system comprising: (a) a camera having at least one CMOS detector and operatively configured to capture at least about 300 or more images per second, (b) a plurality of sensors positioned to detect movement of the microscope slide in x-y-z space during capture of each image, and a processor operatively configured to process images from the camera and data from the plurality of sensors and to correct for movement of images during image capture by either altering the images or discarding the same.

DETAILED DESCRIPTION OF THE INVENTION

Figure 1:
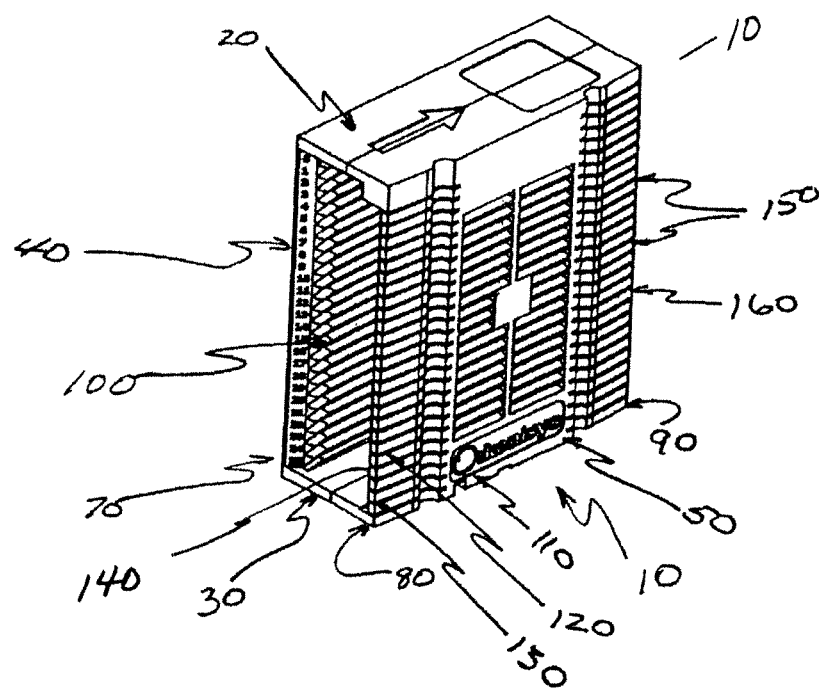
FIG. 1 is a perspective view of an embodiment of the slide magazine.
Figures 2, 3:
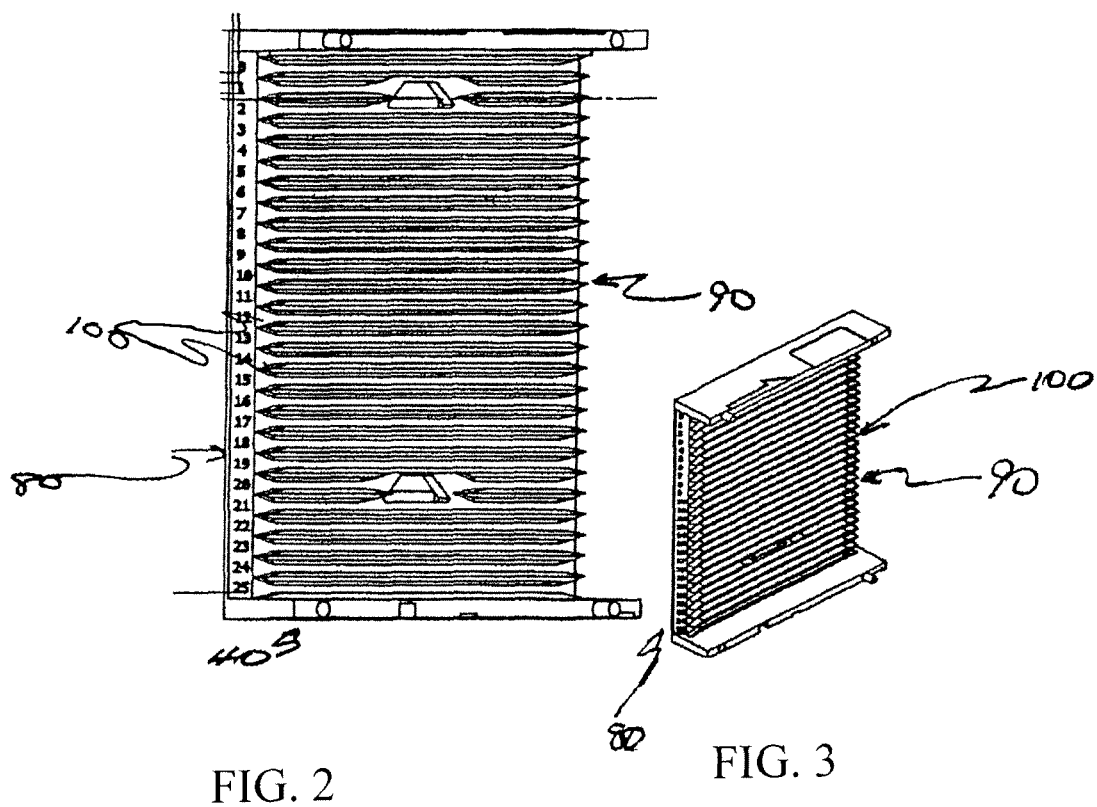
FIG. 2 is a schematic presentation of the inner surface of the first side wall.
FIG. 3 is a perspective view of the first side wall.
Figures 4, 5:
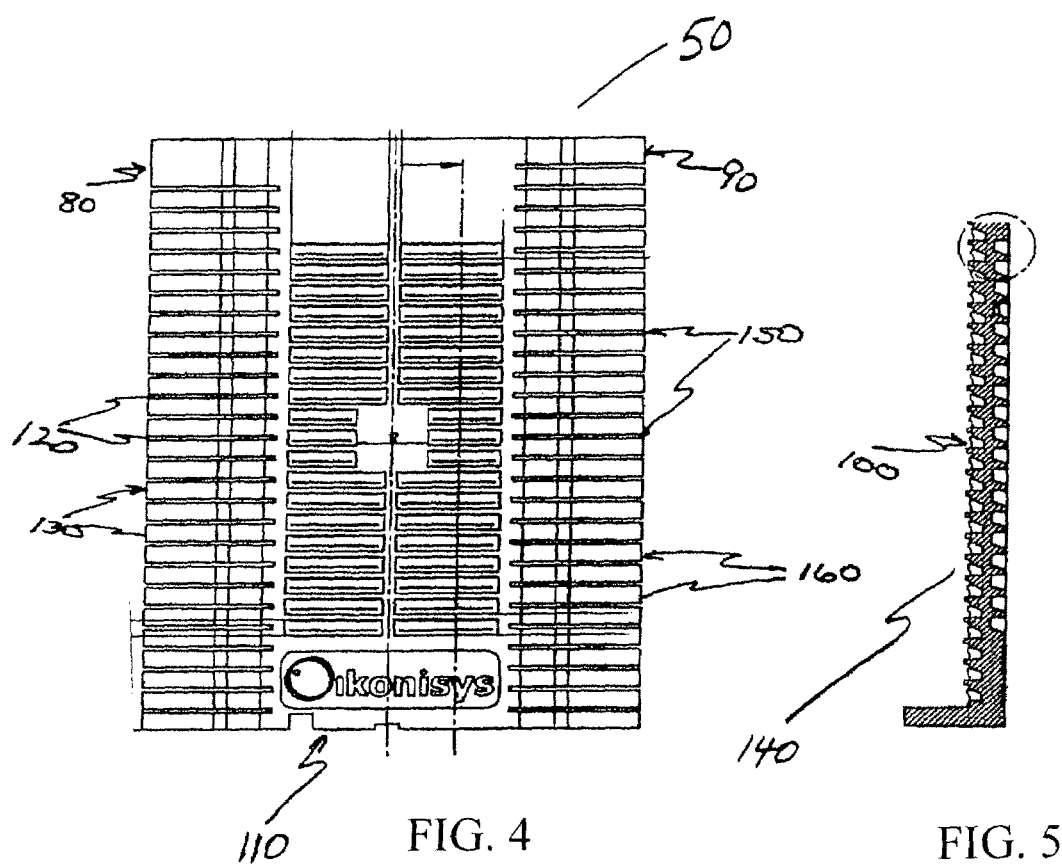
FIG. 4 is a schematic view of the outer surface of the second side wall.
FIG. 5 is an end view of the second side wall showing the rail structure.

Images gained by the microscopy system may be presented to a viewer through a graphical user interface. In one embodiment, there is disclosed a graphical user interface in a microscopy system comprising: (a) a first portion graphically displaying the surface of a microscope slide and the relative position of field of interest thereon; (b) a second portion graphically displaying the field of interest in a plurality of magnifications; wherein the first and second graphical displays are movable at least along the x and y axis.

In one embodiment there is disclosed microscope slides having encoded in digitally readable fashion thereon information pertaining to the origin and desired processing of the tissue sample thereon. Encoding of the data on the slide may be by any suitable means. Examples of such means include recording the data in the form of bar codes, whether one- or two-dimensional (or otherwise), in the form of optical disuniformities representative of digital data (e.g. in the form of pits and lands such as found on a CD or DVD), or stored in an electronic tag on the slide (such as with RFID, or other computer chip). The slide data encodation process may be selected so as to allow encoding of data on the fly in order that information thought useful for processing could be added to the slide as it is moved along the custody chain. For example, with respect to a slide containing tissue from a patient, the encoded microscope slide might contain information including the name, address, age, sex, race, medical history of the patient, and may contain a clinical description of the physician ordered test, as well as information pertaining to the physician who requested the test, and the physician or testing facility where the information obtained from the tests are to be forwarded. As the slide is read, preferably the means for storing data on the slide allows for information from the slide read to be added to the slide for future reference (for example, the date on which the slide was read, by what means the slide was read (e.g. automated microscopy system, the clinic that did the read, the results of the read). The encode data may also comprise information pertaining to the protocol selected for analysis of the material on the slide, and may store one or more images obtained with respect to the sample at points in time. Such images may be useful for adjudging degradation of sample. The data may be stored in a write-once read-many (WORM) memory for purposes of preventing overwriting of stored data or images or, alternatively, in a memory that permits in whole or part overwriting of data. An embodiment may permit the overwriting of only select portions of the stored data.

The encodation on the slides on the cassette may be used to associate the slide with the particular position in the magazine the slide was originally placed. Using such information, when automated microscopy is used, the slide can be read, and the slide replaced in the same position in the magazine, e.g. between the same engagement structures in which it was once held.

When a set protocol for analysis has been provided for processing the slide, an automated method for review of the slide may be undertaken. In one embodiment there is disclosed a method in a computer system for automating microscopic analysis of a plurality of data-encoded microscope slides having material of analytical interest deposited thereon, and stored in a slide cassette, the method comprising: (a) determining the number and position of microscope slides stored in cassette; (b) causing one or more of slides in cassette to be removed from cassette; (c) downloading encoded data on each of slide(s) removed from cassette; (d) associating downloaded encoded data with a set protocol for analysis of material on microscope slide. The encoded data may comprise data physically stored on the slide, or in electronics associated with the slide.

In order to improve efficiency in the microscopic read, slides may be stored in a slide magazine or cassette. The magazine may be an improved magazine 10 allowing for the ease of withdrawal of the slide from the magazine. For example, the slide magazine may comprise a housing having a top wall 20, a bottom wall 30, a first side wall 40 and a second side wall 50 configured as a rectangular box-like structure enclosing a void 70 having a forward edge 80 and a rearward edge 90. Each wall of the structure has an inner surface facing the void and an outer surface facing outward. The inner surface of the first side wall 40 incorporates a plurality of equally spaced rails 100 parallel to the bottom wall extending generally from the forward edge 80 to the rearward edge 90. The second side wall 110 is partially cut with equally spaced slots 120, parallel to the bottom wall 30 forming flexible fingers 130, extending from the forward edge 80 partially to the rearward edge 90. The inner surface of the second side wall 50 incorporates a second set of rails 140 which are co-planar to the rails 100 located on the first side wall. Each of the second side wall rails 140 may be incorporated, in part, into one of the flexible fingers 130. The spacing between the first side wall 40 and second side wall 50 inner surfaces is selected so that when a microscope slide is inserted into magazine 10, so as to sit on the corresponding first 100 and second 140 wall surface rails, the respective flexible finger 130 is displaced resulting in the application of a securing force on the slide. The second side wall 50 may optionally also be partially cut to result in a second set of equally spaced slots 150, in co-planar alignment with the first set of slots 120, parallel to the bottom wall 30 forming flexible fingers 160, extending from the rearward edge 90 partially to the forward edge 80. The flexible fingers 130, 160 structure may provide for click lock of the microscope slide into its respective parking position. Thus dislodgement of the microscope slides from the magazine may be prevented irrespective of spatial orientation.

In operation, the microscope slide is placed entirely within said void between a spaced rail of said inner surface of said first side wall and a spaced rail of said inner surface of said second side wall, said microscope slide is locked in place within the magazine by a snap-fit engagement structure associated with at least one flexible finger. One example of a snap-fit engagement structure is a discontinuity on the surface of the finger.

When slides are stored in magazines 10 or cassettes and the magazines/cassettes are loaded onto an automated microscopy system, it is advantageous that the microscopy system have a slide feeder that is optimized for the magazine/cassette.

In one embodiment of the invention, the slides are removed from the magazine 10 by a slide feeder (not shown) that removes the slide from the magazine 10 by grabbing the slide along the two lateral surfaces of the slide, that is, holding the slide by pressure fit at the slides. Such system is advantageous in that it reduces the risks of introducing artifacts into the sample view (e.g. by scratching the slide from beneath, adding dust to the portion of the slide to be read etc.). In one embodiment, there is disclosed a slide feeder for moving a slide having a top surface, a bottom surface and two or more lateral side surfaces(s) from a first location to a second location, the slide feeder comprising: (a) a stage operatively configured to move in an x-y direction; and a slide engager coupled to the stage, the slide engager operatively configured to hold the slide by pressure fit between two or more lateral surfaces of the slide.

The slide feeder may then position the slide for read in the stage. In one embodiment, there is provided a microscope for reading a microscope slide, the microscope comprising: (a) a first stage operatively configured to hold a microscope slide and to move only along an x-y axis; (b) a second stage operatively associated with the first stage capable of movement only along the z axis; wherein movement of the second stage along such axis causes movement of the microscope slide held by the first stage in the same direction.

Particularly when automated microscopy is employed wherein the system is designed to provide an automated diagnosis with respect to a tissue sample from a patient, it is advantageous to obtain multiple images of a sample. In one embodiment, there is provided microscope slide image capture system comprising: (a) a camera having at least one CMOS detector (or other suitable imaging detector such as, for example, CCD) and operatively configured to capture, for example, at least about 300 or more images per second; (b) a plurality of sensors positioned to detect movement of the microscope slide in x-y-z space during capture of each image; and a processor operatively configured to process images from the camera and data from the plurality of sensors and to correct for movement of images during image capture by either altering the images or discarding the same.

Images obtained may be displayed in numerous manners to a microscopist interested in reviewing the images, in particular to confirm the tentative diagnosis of an automated microscopy system. In one embodiment, there is disclosed a graphical user interface in a microscopy system comprising: (a) a first portion graphically displaying the surface of a microscope slide and the relative position of field of interest thereon; (b) a second portion graphically displaying the field of interest in a plurality of magnifications; wherein the first and second graphical displays are movable at least along the x and y axis.

In an embodiment, a processor configured for processing information from said detector and said field objective may be employed to determine the position of the field viewed or desired to be marked with respect to at least one of the said electronically-addressable position tag(s). The processor may also write the position of the field desired to be marked in response to said reference position tag in electronic data memory associated with said slide. The processor may further write the image of the microscope field to said electronic data memory associated with said slide.

Once images are evaluated, it may be useful clinically to once more view the particular slide, which is the basis of the tentative diagnosis. In order to home back into the particular cell or area of the slide, which raises suspicions, it is useful to have a system that allows for rapid pinpointing of the exact cell or area. One method for doing so, proposed herein, utilizes one or more tags on the microscope slide, which act as reference point(s) on the slide to provide for "GPS-like" repositioning of the objective of the microscope with the particular area on the slide to be viewed. The reference tags should be automatically detectable and be correlated with a particular reference position on the slide. By calculating position of each image with respect to one or more such tags on the slide, and storing the same with the image, one can quickly return to the original field of view on the slide. This eliminates the need to repeat the search over the entire specimen to locate the field of interest.

In one embodiment there is disclosed an automated microscope slide analysis system for viewing microscope slides, the system comprising: (a) one or more microscope slides having one or more electronically-addressable position tag(s) thereon; (b) a field objective operatively configured to allow viewing of a defined field on microscope slide; (c) an emitter operatively configure to emit an electromagnetic wave toward at least one of electronically-addressable position tag(s); (d) a detector operatively configured to detect at least one of position tag(s) from the response of the tag to the electromagnetic wave; and a processor configured for processing information from the detector and the field objective to determine the position of the field viewed or desired to be marked with respect to at least one of the electronically-addressable position tag(s).

STATEMENT REGARDING PREFERRED EMBODIMENTS

While the invention has been described with respect to preferred embodiments, those skilled in the art will readily appreciate that various changes and/or modifications can be made to the invention without departing from the spirit or scope of the invention as defined by the appended claims. All documents cited herein are incorporated by reference herein where appropriate for teachings of additional or alternative details, features and/or technical background.

What is claimed:

1. An automated microscope slide analysis system for viewing or imaging microscope slides, said system comprising:
   one or more microscope slides each having one or more electronically-addressable reference position tag(s) thereon;
   a field objective operatively configured to allow viewing or imaging of a defined field on said microscope slide;
   an emitter operatively configured to emit an electromagnetic wave toward at least one of said electronically-addressable reference position tag(s);
   a detector operatively configured to detect said position tag from response of said position tag to said electromagnetic wave; and
   a processor configured for processing information from said detector and said field objective to determine a position of a field viewed or desired to be marked with respect to at least one of the said electronically-addressable position tag(s), and to cause writing of said position of said field desired to be marked in response to said reference position tag in electronic data memory associated with said slide.

2. An automated microscope analysis system of claim 1 wherein said processor is further configured to cause writing of an image to said electronic data memory associated with said slide.

3. An automated microscope analysis system of claim 1 wherein said electronically-addressable reference position tag is a radio frequency identification device (RFID).

4. An automated microscope analysis system of claim 1 wherein said electronic data memory is write once read many (WORM) memory.

5. An automated microscope slide analysis system, in accordance with claim 1, further comprising:
   a camera having at least one image detector and operatively configured to capture multiple images per second;
   said electronically-addressable reference position tag(s) are further operatively configured to detect movement of said microscope slide in x-y-z space during capture of each image;
   said processor is further operatively configured to process said captured images from said camera and data from said electronically-addressable reference position tag(s) and to correct for movement during image capture by either altering said captured images or discarding said captured images.

6. An automated microscope slide analysis system, in accordance with claim 5, wherein said camera has at least one CMOS detector.

7. A microscope slide image capture system of claim 5 wherein the said camera has at least one CCD detector.

8. A microscope slide image capture system of claim 5 wherein said camera is operatively configured to capture at least about 300 or more images per second.

* * * * *